United States Patent [19]

Tanskanen

[11]  4,347,236
[45]  Aug. 31, 1982

[54] PROCESS FOR THE PREPARATION OF A MIXTURE OF AN ANTI-INFLAMMATORY STEROID AND A FLUORO-CHLORO-HYDROCARBON TO BE USED AS A PROPELLANT

[75] Inventor: Paavo T. Tanskanen, Kuopio, Finland

[73] Assignee: Orion-yhtymä Oy, Finland

[21] Appl. No.: 265,333

[22] Filed: May 19, 1981

[30] Foreign Application Priority Data

May 19, 1980 [FI] Finland .................................. 801610

[51] Int. Cl.³ ......................... A61L 9/04; A61K 31/56
[52] U.S. Cl. ....................................... 424/45; 424/243
[58] Field of Search .................................. 424/45, 243

[56] References Cited

U.S. PATENT DOCUMENTS 4,225,597  9/1980  Finckenor .......................... 424/243

OTHER PUBLICATIONS

Brown et al., "British Medical Journal", Mar. (1972), No. 1, pp. 585–590.

Primary Examiner—Elbert L. Roberts
Attorney, Agent, or Firm—Burns, Doane, Swecker & Mathis

[57] ABSTRACT

A process by means of which an increase in the particle size of a micro-ground anti-inflammatory steroid in the aerosol propellant is prevented. The increase in the particle size is prevented at the suspending stage when the solubility of the steroid into the propellant is reduced by using a low temperature and by initially mixing only a little quantity of the propellant with the steroid. If desired, the smallest and dissolved steroid particles can be removed by filtering. The particle size does not become larger even afterwards when the suspension is allowed to be stabilized for a sufficiently long time before the temperature is raised or the rest of the propellant is added.

17 Claims, No Drawings

PROCESS FOR THE PREPARATION OF A MIXTURE OF AN ANTI-INFLAMMATORY STEROID AND A FLUORO-CHLORO-HYDROCARBON TO BE USED AS A PROPELLANT

The subject of the present invention is a process for the preparation of a mixture of an anti-inflammatory steroid, such as beclomethasone dipropionate ground into a particle size smaller than 5 µm, and of a fluoro-chloro-hydrocarbon to be used as a propellant, such as trichlorofluoromethane or dichloro-difluoromethane. The process in accordance with the invention is characterized in that the detrimental increase in the particle size of the steroid is prevented by suspending the steroid at a temperature of about +5 ... −40° C. into a little quantity of the propellant, by stirring the mixture for at least 24 hours, and by adding the necessary quantity of the propellant during or after the stirring. The mixture is stirred preferably for 1 to 3 days. Moreover, if desired, it is possible to filter the portion of the steroid that has the smallest particle size and that has been dissolved, off the mixture.

In mixtures prepared by means of the process in accordance with the invention, increase in the size of the crystals does not take place during storage either. Therefore they are suitable for use in aerosol preparations intended to be administered into the respiratory canals, in which preparations the active agent must be sufficiently finely divided in order to be able to be carried right into the area of the little bronchi.

From the British Pat. No. 1,429,184 it is known that beclomethasone dipropionate or some other corticosteroids which have been ground into a particle size suitable for inhalation, e.g. 2 to 5 µm, in the fluorochlorohydrocarbons used as aerosol propellants form rather large crystals or crystal agglomerations, larger than 20 µm. Particles of such a large size are not carried deep enough into the lungs.

In the above patent publication, the observation is also stated that, when the produced large crystals are ground back into the desired smaller crystal size, the crystals no longer become larger to a substantial extent. It is on this observation that the process in accordance with the said patent for the preparation of steroids of a sufficiently stable crystal size is based. According to the process, the crystals are first allowed to grow freely, possibly by means of recrystallisation, whereupon they are ground, e.g., in a ball mill to the desired crystal size. It may be necessary to remove the propellant before grinding, in which case the steroid must, of course, be suspended again into the propellant after the grinding.

In the grinding of a crystalline material, a considerable part of the material may be converted into a higher-energy, amorphic state. The growth of the steroid particles in fluoro-chlorohydrocarbons will be mainly due to the circumstance that the higher-energy, amorphic material tends to be dissolved and recrystallised into a lower-energy, organized stable state. The dissolution is favoured by the small size of the particles.

In a stable suspension of a steroid and a fluoro-chlorohydrocarbon, medium has been adsorbed uniformly on the surface of the solid particles. A kind of a "solvate" has been formed which prevents a growth of the crystals via dissolution and recrystallisation (cf. Finnish Pat. No. 53,067).

According to the present invention, stable suspensions can be prepared without increasing the particle size so that the dissolution of the steroid is reduced essentially during the stirring step. The dissolution is reduced by working at a low temperature (about −10° to −30° C.) and by first mixing the steroid into a little quantity of propellant (e.g., 1 to 10% of the whole quantity). Attempts are made to perform the moistening of the steroid as uniformly as possible in order that no concentration gradients could be formed in the mixture. After the stabilization stage propellant can be added without an increase in the particle size. If desired, dissolved steroid can be removed by filtering by means of a membrane filter, at which time, when dissolving and mixing, it is possible to work at a higher temperature (about +5° to −10° C.).

The process in accordance with the invention is industrially highly usable. By its means it is possible to prepare suspensions suitable for aerosol preparations by one unit operation, stirring, without having to perform a possible dissolution and recrystallisation or grinding. Grinding is not a recommendable operation in this connection, because it—besides increasing the work—may convert part of the material into excessively small or high-energy, amorphic particles, which may cause new growth of crystals. Moreover, too small and light particles are not recommendable even therefore that they do not settle easily from the breathing air onto the surface of the lungs.

An aerosol product prepared by means of the process in accordance with the invention, described in example 1, was compared with a product prepared by means of a conventional process.

The reference product was prepared as follows: 1.05 grams of micro-ground beclomethasone dipropionate was suspended into 403 grams of trichloro-fluoromethane at +15° C., 0.12 g of oleic acid was added, and the mixture was stirred for 6 hours, the temperature being still +15° C. 4.04 grams of the suspension were dosed into a can and the can was closed by means of a dose valve. 10.36 grams of dichloro-difluoromethane was added into the can by means of pressure.

The distribution of the particle size was determined out of the products immediately on preparation as well as after 1, 3, 42, and 61 days. On the basis of the distribution of the particle size, an average particle size based on the weight was calculated for each sample.

The results of the comparative test are given in the following table.

| Days after filling of can | Average particle size/µm | | | | |
|---|---|---|---|---|---|
| | 0 | 1 | 3 | 42 | 61 |
| Product as per invention | 1.3 | 2.6 | 2.3 | 2.2 | 2.4 |
| Reference product | 1.9 | 6.2 | 13.9 | 19.4 | 21.9 |

During a storage of 61 days, the particle size of the product in accordance with the invention was not increased substantially, whereas the particle size of the reference product became about 10-fold.

The following examples illustrate the invention.

EXAMPLE 1

1.05 g beclomethasone dipropionate was suspended into 40 g trichloro-fluoromethane at −25° C. The mix was stirred by means of a magnetic agitator at −25° C. for 3 days. The suspension was mixed into 362.8 g of trichloro-fluoromethane that had been cooled to +5°

C., 0.12 g oleic acid was added, and the mix was stirred for another 0.5 hours. 4.04 g of the suspension prepared in this way was dosed into a can, the can was closed by means of a dose valve, and through the valve, 10.36 g dichloro-difluoromethane was added by means of pressure.

EXAMPLE 2

1.05 g beclomethasone dipropionate and 4.0 g trichloro-fluoromethane were mixed at −20° C. To the mixture, trichloro-fluoromethane that had been cooled to −20° C. was added as small quantities so that during the first 6 hours 36.0 g were added, during the next 12 hours 160 g, and during the next 18 hours 202.8 g.

EXAMPLE 3

0.5 g beclomethasone dipropionate was added to dichloro-difluoromethane of −35° C. (about 20 grams). The mix was stirred for 2.5 days at −25° C. in a tightly sealed pressure-proof vessel by means of a magnetic agitator. The dichloro-difluoromethane was evaporated off. 200 g trichloro-fluoromethane were added. The mix was stirred at the room temperature for 4 hours.

EXAMPLE 4

3.15 g beclomethasone dipropionate was suspended at +5° C. into 150 ml trichloro-fluoromethane, the mix was stirred for 1 hour, and 120 ml trichloro-fluoromethane was removed by filtering by means of a 0.45 μm Millipore, filter, and a corresponding quantity of pure trichloro-fluoromethane was added. The stirring, filtering, and addition were repeated 3 times. After the last time stirring was continued for 36 hours, whereupon trichloro-fluoromethane was added ad 1200 g. The temperature was all the time +5° C.

What is claimed is:

1. A process for preparing a stable aerosol formulation of beclomethasone dipropionate in a fluoro-chlorohydrocarbon propellant wherein the beclomethasone dipropionate has a particle size smaller than 5 μm, said process comprising suspending beclomethasone dipropionate, ground into a particle size smaller than 5 μm, in a small quantity of a fluoro-chlorohydrocarbon propellant at a temperature of from about −40° to +5° C., stirring the resultant mixture for at least 24 hours at a temperature of from about −40° to +5° C. in the course of which time the mixture is brought to the stabilization stage, and adding to the stabilized mixture during or after said stirring a further quantity of the propellant sufficient to make an aerosol formulation suitable for use in inhalation therapy, whereby increase in the particle size of the beclomethasone dipropionate is substantially prevented throughout said process and during subsequent storage.

2. A process as claimed in claim 1, wherein the fluoro-chloro-hydrocarbon propellant is trichlorofluoromethane or dichlorodifluoromethane.

3. A process as claimed in claim 1 or 2, wherein the mixture is stirred for 1 to 3 days.

4. A process as claimed in claim 1 or 2, wherein the beclomethasone dipropionate is suspended in the propellant at a temperature of from about −40° to −10° C.

5. A process as claimed in claim 3, wherein the beclomethasone dipropionate is suspended in the propellant at a temperature of from about −40° to −10° C.

6. A process as claimed in claim 1, wherein the beclomethasone dipropionate is suspended in trichlorofluoromethane at a temperature of from about −25° to −15° C.

7. A process as claimed in claim 1, wherein the beclomethasone dipropionate is suspended in dichlorodifluoromethane at a temperature of from about −35° to −25° C.

8. A process as clamed in claim 1 or 2, wherein the suspension is filtered during the stirring stage by means of a membrane filter of 0.2 to 0.5 μm.

9. A process as claimed in claim 3, wherein the suspension is filtered during the stirring stage by means of a membrane filter of 0.2 to 0.5 μm.

10. A process as claimed in claim 8, wherein the beclomethasone dipropionate is suspended in the propellant at a temperature of from about −10° to +5° C.

11. A process as claimed in claim 9, wherein the beclomethasone dipropionate is suspended in the propellant at a temperature of from about −10° to +5° C.

12. A process as clamed in claim 9, wheein the beclomethasone dipropionate is suspended in the propellant at a temperature of from about 0° to +5° C.

13. A process as claimed in claim 9, wherein the beclomethasone dipropionate is suspended in the propellant at a temperature of from about 0° to +5° C.

14. A process as claimed in claim 1, 2 or 6, wherein the quantity of propellant used in the suspending stage is 1 to 10 percent by weight of the total quantity of propellant.

15. A process as claimed in claim 11, wherein the quantity of propellant used in the suspending stage is 1 to 10 percent by weight of the total quantity of propellant.

16. A process as claimed in claim 4, wherein the quantity of propellant used in the suspending stage is 1 to 10 percent by weight of the total quantity of propellant.

17. A process as claimed in claim 5, wherein the quantity of propellant used in the suspending stage is 1 to 10 percent by weight of the total quantity of propellant.

* * * * *